(12) United States Patent
Hauck et al.

(10) Patent No.: US 8,265,745 B2
(45) Date of Patent: Sep. 11, 2012

(54) CONTACT SENSOR AND SHEATH EXIT SENSOR

(75) Inventors: John A. Hauck, Shoreview, MN (US); Jeffrey A. Schweitzer, St. Paul, MN (US); Kenneth H. Drew, Brooklyn Park, MN (US)

(73) Assignee: St. Jude Medical, Atrial Fibillation Division, Inc., St. Paul, MN (US)

( * ) Notice: Subject to any disclaimer, the term of this patent is extended or adjusted under 35 U.S.C. 154(b) by 708 days.

(21) Appl. No.: 11/618,484

(22) Filed: Dec. 29, 2006

(65) Prior Publication Data
US 2008/0255470 A1    Oct. 16, 2008

(51) Int. Cl.
*A61B 5/05* (2006.01)
(52) U.S. Cl. ........................................ 600/547; 600/587
(58) Field of Classification Search .................. 600/547, 600/587
See application file for complete search history.

(56) References Cited

U.S. PATENT DOCUMENTS

| | | | |
|---|---|---|---|
| 4,280,503 A * | 7/1981 | Ackerman | 607/9 |
| 5,341,807 A | 8/1994 | Nardella | |
| 5,944,022 A * | 8/1999 | Nardella et al. | 128/899 |
| 6,197,021 B1 * | 3/2001 | Panescu et al. | 606/31 |
| 6,569,160 B1 * | 5/2003 | Goldin et al. | 606/41 |
| 6,714,806 B2 | 3/2004 | Iaizzo et al. | |
| 6,939,313 B2 * | 9/2005 | Saadat et al. | 600/587 |
| 6,951,549 B1 * | 10/2005 | Beyerlein | 604/117 |
| 6,955,675 B2 * | 10/2005 | Jain | 606/41 |
| 2003/0199817 A1 * | 10/2003 | Thompson et al. | 604/95.01 |

FOREIGN PATENT DOCUMENTS

WO    WO-2007/067941    6/2007

OTHER PUBLICATIONS

"Supplementary European Search Report and Opinion", EP Patent Application No. 07 864 391.3 Mar. 7, 2011.

* cited by examiner

*Primary Examiner* — Max Hindenburg
*Assistant Examiner* — Renee Danega
(74) *Attorney, Agent, or Firm* — Marsh Fischmann & Breyfogle LLP

(57) ABSTRACT

A system and method is provided that allows for determining the local impedance of one or more electrodes of an electrode catheter. Such local impedance may be utilized to identify the relative position of an electrode catheter to a sheath of a guiding introducer. In another arrangement, local impedance of a catheter electrode can be utilized to calibrate a catheter electrode to provide improved contact sensing.

20 Claims, 10 Drawing Sheets

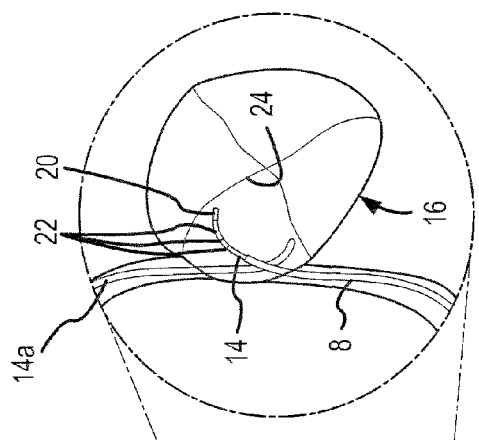
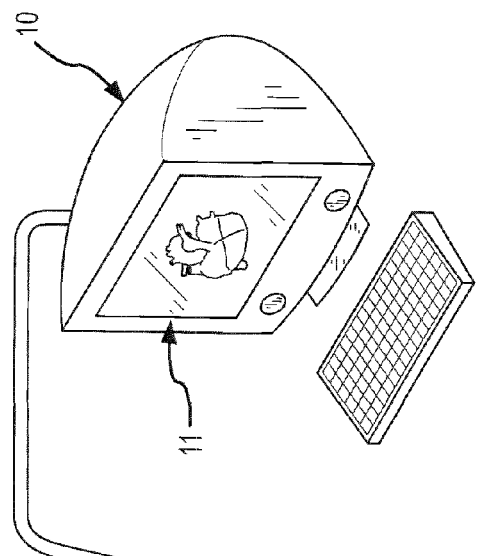
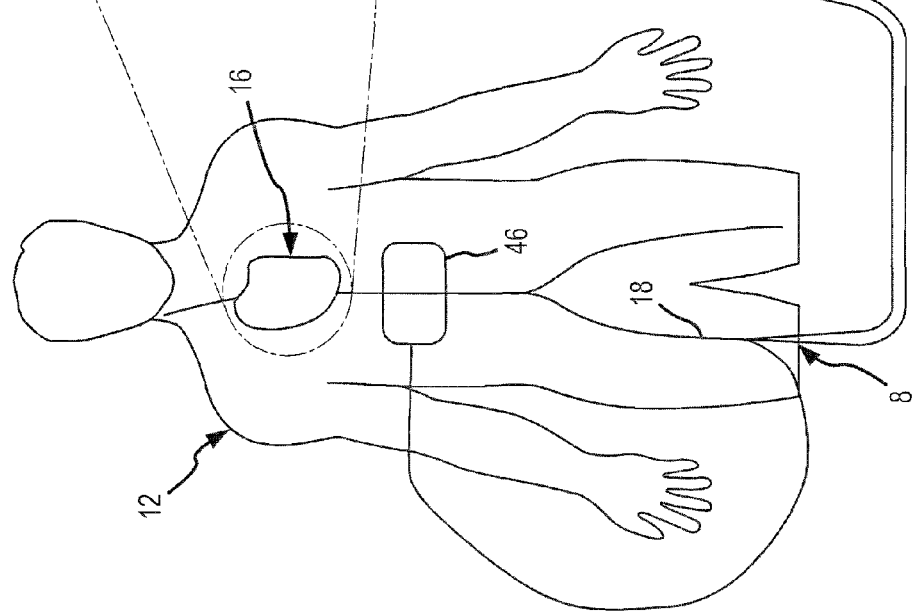
FIG. 1a
FIG. 1

CONTACT SENSOR AND SHEATH EXIT SENSOR

BACKGROUND OF THE INVENTION a. Field of the Invention

The instant invention is directed toward an electrode catheter and a method for using the electrode catheter for tissue mapping, guidance and/or tissue ablation. In particular, the electrode catheter of the present invention may assess electrode location relative to an insertion sheath and/or assess electrode-tissue contact.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is typically inserted into a vessel near the surface of the body and is guided to a specific location within the body for examination, diagnosis, and treatment. For example, catheters can be used to convey an electrical stimulus to a selected location within the human body, e.g., for tissue ablation. In addition, catheters with sensing electrodes can be used to monitor various forms of electrical activity in the human body, e.g., for electrical mapping.

Catheters are used increasingly for medical procedures involving the human heart. Typically, the catheter is inserted in an artery or vein in the leg, neck, or arm of the patient and threaded, sometimes with the aid of a guide wire or introducer, through the vessels until a distal tip of the catheter reaches the desired location for the medical procedure in the heart. In the normal heart, contraction and relaxation of the heart muscle (myocardium) takes place in an organized fashion as electro-chemical signals pass sequentially through the myocardium.

Sometimes abnormal rhythms occur in the heart, which are referred to generally as arrhythmia. The cause of such arrhythmia is generally believed to be the existence of an anomalous conduction pathway or pathways that bypass the normal conduction system. These pathways are usually located in the fibrous tissue that connects the atrium and the ventricle.

An increasingly common medical procedure for the treatment of certain types of cardiac arrhythmia is catheter ablation. During conventional catheter ablation procedures, an energy source is placed in contact with cardiac tissue (e.g., associated with a anomalous conduction pathway) to heat the tissue and create a permanent scar or lesion that is electrically inactive or noncontractile. The lesion partially or completely blocks the stray electrical signals to lessen or eliminate arrhythmia.

Ablation of a specific location within the heart requires the precise placement of the ablation catheter within the heart. Precise positioning of the ablation catheter is especially difficult because of the physiology of the heart, particularly because the heart continues to beat throughout the ablation procedures. Commonly, the choice of placement of the catheter is determined by a combination of electrophysiological guidance and computer generated maps/models that may be generated during a mapping procedure. Accordingly, it is desirable that any map or model of the heart be as accurate as practicable.

Several difficulties may be encountered, however, when attempting to form lesions at specific locations using some existing ablation electrodes. One such difficulty encountered with existing ablation electrodes is how to ensure adequate tissue contact and/or electrical coupling. Electrode-tissue contact is not readily determined using conventional techniques such as fluoroscopy. Instead, the physician determines electrode-tissue contact based on his/her experience using the electrode catheter. Such experience only comes with time, and may be quickly lost if the physician does not use the electrode catheter on a regular basis. In addition, attempts to directly measure contact between an electrode and target tissue are often subject to local variations in the surrounding media. Such variation can distort such measurement, which can lead to false electrode-tissue contact indications.

BRIEF SUMMARY OF THE INVENTION

Generally, it has been recognized that the environment surrounding a catheter electrode alters the electrical properties of the electrode in response to an applied electrical signal. For instance, the impedance may vary, or a value related to impedance or impedance components may otherwise vary, between an electrode that is within a confined/small volume structure (e.g., a sheath or vessel) and the same electrode in a structure having a larger volume. That is, the surrounding fluid of small volume structure may have different electrical properties (e.g., based on flow rates etc.) than the electrical properties surrounding fluid of a larger volume. These different electrical properties alter the local electrical response of the electrode fluid interface. Accordingly, it has been recognized that changes of such local responses may be utilized to provide useful information that can be utilized to, for example, provide improved sensing during mapping and/or provide improved tissue contact sensing.

In one arrangement, local responses of a catheter may be utilized to identify the relative position of an electrode catheter to a sheath of a guiding introducer. In another arrangement, local responses of a catheter electrode can be utilized to calibrate a catheter electrode to provide improved contact sensing.

According to one aspect, a system and method is provided for sensing when an electrode of a catheter passes between a constricted area and a less constricted area. For example when the catheter passes into and/or out of a sheath of an introducer or when the catheter passes into or out of a blood vessel. Initially, an introducer may be guided to an internal tissue location of interest such as the heart. The introducer may provide an internal channel or lumen to the tissue area of interest. Accordingly, a catheter may be disposed through the internal channel to access the tissue area. In conjunction with moving the catheter relative to the introducer, an electrical signal may be provided to one or more electrodes associated with the catheter. Accordingly, by monitoring a response of these one or more electrodes, a change in the response may be identified that is indicative of the electrode at least partially passing between a constricted area and a less constricted area. Accordingly, upon identifying a change in the response, an output may be generated that is indicative of this change of response.

Identifying a change in the response may include measuring an impedance of the electrode in response to the electrical signal. In such an arrangement, the impedance may be measured at a series of times to identify changes therein. For instance, an initial impedance may be measured for the electrode when the electrode is at a first position, which may be known to be within the internal channel of the introducer or disposed in a fluid or blood pool away from a wall of internal tissue area. Accordingly, as the location of the electrode changes, a subsequent impedance measurement may be obtained. These impedance measurements may be compared to identify a change between the initial impedance and the subsequent impedance. Likewise, if the change between the initial and subsequent impedances is greater than a predetermined threshold, which may be based on stored information, an output may be provided to a user indicating the change. Further, the change in impedance may be utilized to identify local variances of surrounding media (e.g., blood) such that the electrode may be calibrated for subsequent tissue contact.

In a further arrangement of the present aspect, the catheter may include at least first and second electrodes. For instance, the catheter may include a tip electrode and a ring electrode or a plurality of ring electrodes. In such an arrangement, impedances of the tip electrode and one or more of the ring electrodes may be monitored. If the surrounding environment of one of the electrodes changes, for example, caused by moving the catheter, a change in the response of one of the electrodes may occur without a corresponding change in the other electrode. Accordingly, such a change in the relative responses may be utilized to identify the passage of one of the electrodes into or out of the introducer or into or out of an internal structure such as a vein or artery.

According to another aspect, a system and method is provided for use in calibrating an electrode catheter as well as assessing contact between an electrode and tissue. The system/method includes guiding a catheter to an internal tissue location, where the catheter includes at least first and second electrodes. First and second electrical signals may be provided to the first and second electrodes, respectively. Accordingly, the relative response of the first and second electrodes may be identified. Further, an output may be generated based on a change in the relative response. For instance, if both electrodes are initially in a blood pool (i.e., heart chamber) and one of the electrodes contacts a wall of the chamber, the impedance of the contacting electrode may change relative to the non-contacting electrode. In contrast, if both electrodes pass into a smaller surrounding area (e.g., a vein or artery), each electrode may experience a change in impedance such that a relative impedance may remain substantially unchanged.

The system and method may include providing first and second signals having equal frequency and phase, wherein an amplitude of one of the first and second signals is adjustable. Such individual adjustment of the amplitude of one of the signals may allow for matching the impedance of the first and second electrodes. In this regard, it will be noted that the resistivity of blood may change during the cardiac cycle. That is, the flow of the blood may change the resistivity and thus the measured impedance by several percent or more. Accordingly, it may be desirable to match the impedances of the electrodes in order to account for dynamic changes in the electrical properties of local media. Stated otherwise, by matching the impedance of the electrodes, the electrode catheter may be calibrated for local conditions. Such calibration may include initially positioning the first and second electrodes at a location within a blood pool (e.g., away from a wall in a heart chamber). The impedances of the first and second sensors may then be matched. Accordingly, common mode noise and impedance may be cancelled between the first and second electrodes thereby accounting for local variances. The catheter may be moved until one of the electrodes contacts the surface. An impedance measurement of the contact may then be obtained that is substantially free of local variance.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 is a diagrammatic illustration of an exemplary catheter system which may be implemented to access internal patient tissue for mapping and/or tissue ablation procedures.

FIG. 1a is a detailed illustration of the patient's heart in FIG. 1, showing the electrode catheter after it has been moved into the patient's heart.

DETAILED DESCRIPTION OF THE INVENTION

Figure 2:
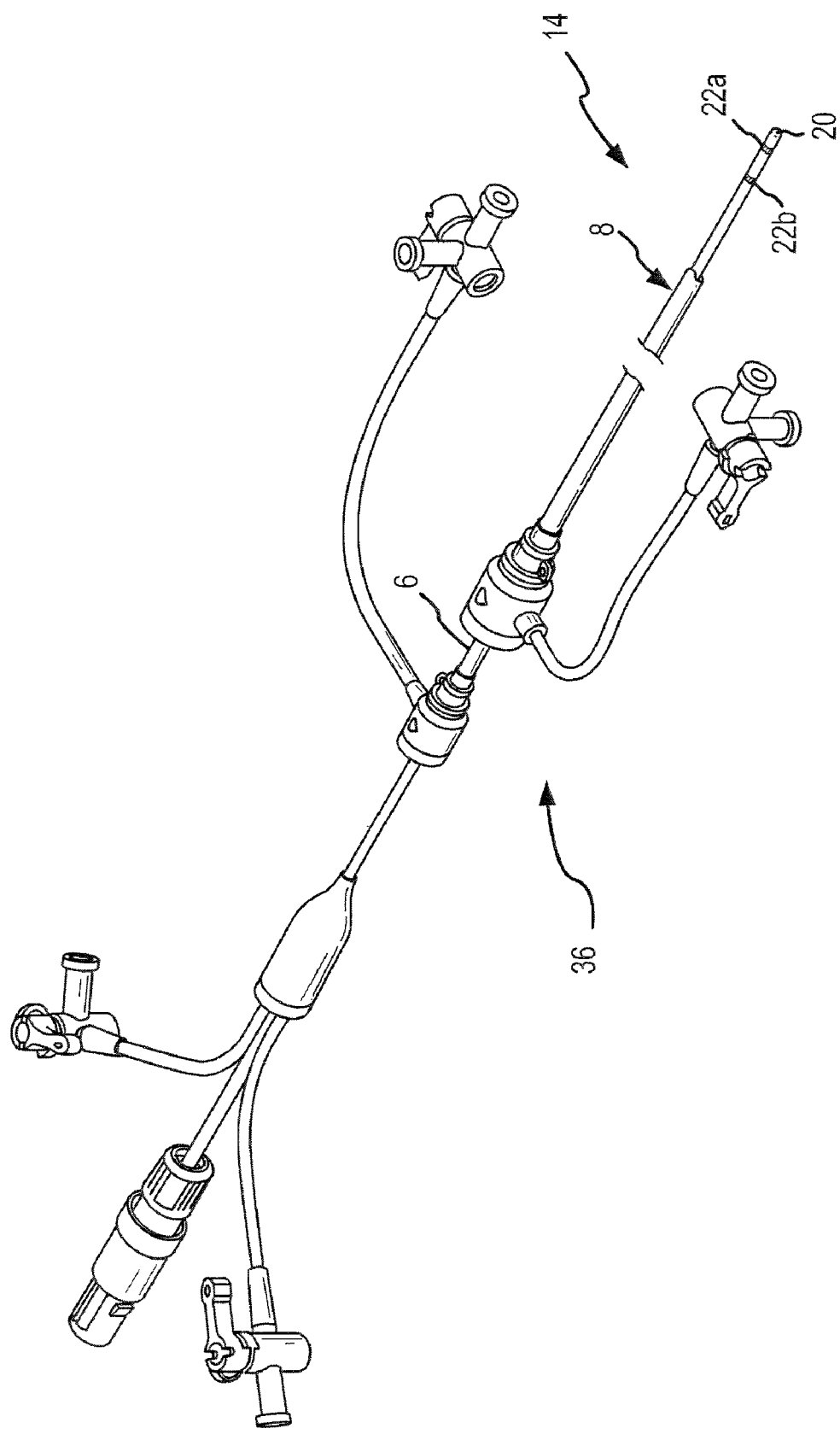
FIG. 2 is an exemplary catheter that may be utilized with the system of FIG. 1

FIG. 1 is a diagrammatic illustration of an exemplary electrode catheter system 10 which may be implemented to assess and map internal patient tissue. Further, the system is operative to assess electrode-tissue contact to assist in performance of a tissue ablation procedure for a patient 12. Catheter system 10 may include a guiding introducer having a sheath 8, which may be inserted into the patient 12. The sheath 8 may provide a lumen for the introduction of a catheter 14 which may be disposed beyond the distal insertion end of the sheath 8, e.g., for forming ablative lesions inside the patient's heart 16. During an exemplary ablation procedure, a user (e.g., the patient's physician or a technician) may insert the sheath of a guiding introducer into one of the patient's blood vessels 18, e.g., through the leg (as shown in FIG. 1) or the patient's neck. The user, guided by a real-time fluoroscopy imaging device (not shown), moves the sheath 8 into the patient's heart 16 (as shown in more detail in FIG. 1a). When the sheath 8 of the guiding introducer reaches the patient's heart 16, the electrode catheter 14 may be extended through a lumen of the sheath 8 such that the electrode catheter 14 may be guided to a desired location within the heart to perform, for example tissue mapping and/or tissue ablation. In tissue mapping procedures, a model of the heart may be generated on an output display 11, which may be utilized for subsequent catheter guidance to perform, for example, an ablation procedure. One or more additional catheters 14a may also be utilized during mapping and/or subsequent procedures.

FIG. 2 illustrates one embodiment of an electrode catheter system 36 with an electrode catheter 14 that may be selectively extended from the distal end portion of the sheath 8 of the guiding introducer. As used herein and commonly used in the art, the term "distal" is used generally to refer to components of the catheter system, such as the tip electrode 20, located toward the insertion end of the of the ablation catheter 14 (i.e., toward the heart or other target tissue when the catheter is in use). In contrast, the term "proximal" is used generally to refer to components or portions of the catheter that are located or generally orientated toward the non-insertion end of the catheter (i.e., away from or opposite the heart or other target tissue when the catheter is in use).

The sheath 8 is a tubular structure defining at least one lumen or longitudinal channel. The sheath 8 is used in conjunction with the catheter 14 to introduce and guide the catheter 14 to the target internal tissue area. The catheter 14, however, may be used alone or with other guiding and introducing type devices depending on the particular procedure being performed. As shown in FIG. 2, the catheter includes a tubular body or shaft 6 extending from the connector, through the sheath 8, and out of the lumen at the distal end of the sheath 8. In one implementation, the sheath 8 and shaft 6 are fabricated with a flexible resilient material. The sheath and the components of the catheter are preferably fabricated of materials suitable for use in humans, such as polymers. Suitable polymers include those well known in the art, such as polyurethanes, polyether-block amides, polyolefins, nylons, polytetrafluoroethylene, polyvinylidene fluoride, and fluorinated ethylene propylene polymers, and other materials. In the particular ablation system configuration of FIG. 2, the sheath 8 is configured to receive and guide the ablation catheter within an internal lumen to the appropriate location in the heart once the sheath is pre-positioned in the appropriate location.

The electrode catheter 14 of the exemplary embodiment includes a tip electrode 20 and a plurality of ring electrodes 22a-n (referred to collectively as electrodes 22). Though shown as utilizing a plurality of ring electrodes, it will be noted that other electrodes may be utilized as well. For instance, spot electrodes or segmented ring electrodes may be utilized. These electrodes 20, 22 may be implemented to electrically map the myocardium 24 (i.e., muscular tissue in the heart wall). In this regard, information from the electrodes may be utilized to a create realistic model of cardiac chamber geometries or models of other internal tissue depending on the particular procedure being performed. As noted, such a model may be displayed on a user output 11 (See FIG. 1) for use in guiding the catheter 14, for example, during an ablation procedure performed after mapping.

To create the model, a 3D location system such as the NavX™ navigation and visualization system of St. Jude Medical may be used. In such a system, two or more external patient electrode patches 46 (only one shown) are applied on one or more locations on the body. An electrical signal is transmitted between the patches, and one or more electrodes of one or more catheter within the heart sense the signal. The system 10 collects electrical data from the catheters and uses this information to track or navigate their movement and construct three-dimensional (3-D) models of the chamber. Additionally a physician may sweep the catheter(s) 14 across the heart chamber during data collection to outline the structures and relay the signals to the computer system, which generates the 3-D model. The resulting model may then be utilized to, for example, guide the catheter 14 to one or more locations in the heart where treatment is needed.

Such a system allows for the creation of detailed internal models at the time of study and/or performance of an internal procedure. This is, the system is operative to generate substantially real-time models. Such a system avoids the possible challenges of imaging technologies that rely on models created prior to a time when an internal procedure is performed. As may be appreciated, such previously created models may not reflect subsequent changes to the modeled tissue such as changes in posture and/or fluid loading.

While providing detailed models of internal tissue structure such as the heart, there are potential drawbacks of modeling systems that transmit electrical signals from one or more external patches to an electrode(s) disposed within tissue of interest. For instance, if a catheter electrode (e.g., tip electrode 20) that is utilized to receive the transmitted electrical signals remains within the sheath 8 during the sampling process, gathered data may be distorted. However, such distorted data may yield a plausible, yet erroneous, model and/or erroneous location of the electrode and catheter on the display of the resulting model. Accordingly, an indicator of the position of the electrode(s) of the catheter relative to the sheath is useful. For instance, an indication of an electrode being at the threshold exit location relative to the sheath may be useful.

It may also be useful to know how far a catheter is extended beyond a sheath in order to determine how to guide the catheter. As will be appreciated, the catheter may be guided by a guide wire(s) that bend/deflect an end portion of the catheter. Based on the compliance of the catheter shaft and the length of the portion extending beyond the sheath, a fulcrum may be determined about which the catheter will bend or deflect. Accordingly, knowledge of the length of the catheter may be helpful for determining how to best approach a tissue area of interest. Further, knowledge of when an electrode (e.g., tip electrode 20 and/or one or more ring electrodes 22) has just exited from the sheath allows the sheath exit site to be registered within a navigation model.

As may be appreciated, markings may be provided on proximal portions of the sheath 8 and/or the shaft 6 of the catheter 14 that may provide an indication of the relative positions of the distal tips of these members. However, due to the bending and or compression of the sheath 8 and/or catheter shaft 6 from routing these members to a tissue area of interest, such markings may not provide an accurate indication of the relative positions of the distal ends of these members. Accordingly, an independent indicator of the distal end of the catheter 14 relative to the distal end of the sheath 8 is desirable.

Such a indication may be provided by dedicated sensors interconnected to the distal ends of the sheath 8 and catheter 14. However, due to the space limitations of guided introducers and catheters, such dedicated sensors may not provide an optimal solution. Presented herein, is a system and method that allows for utilizing one or more existing electrodes of the catheter 14 to provide an indication of the relative position of the distal end of the catheter 14 to the sheath 8. Such an indication may be provided for any catheter that passes through the sheath and includes at least one electrode.

Generally, it has been recognized that the environment surrounding a catheter electrode alters the impedance of the electrode in response to an applied electrical signal. For instance, the impedance may be higher when the electrode is within a confined/small volume structure (e.g., a sheath or vein) as opposed to when the electrode is in a structure having a larger volume. That is, in the small volume structure, there is less surrounding fluid (e.g. blood) than in a larger structure such as a heart chamber. Stated otherwise, the local resistive capacity and/or capacitive capacity of the surrounding blood varies with volume, which alters the local impedance of the electrode fluid interface.

Figure 3A:
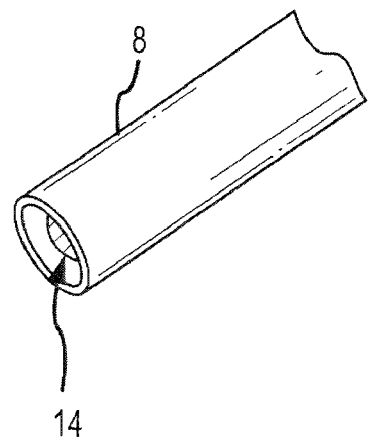
FIGS. 3a-3c are exemplary perspective views of relative positions of an electrode catheter and sheath.
Figure 3B:
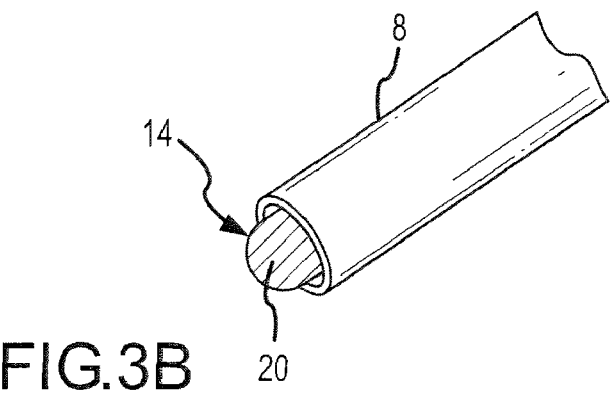
Figure 3C:
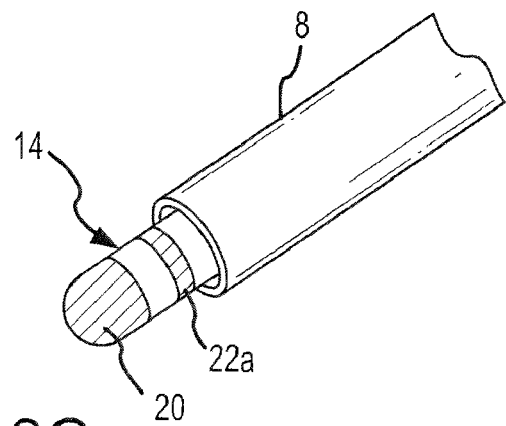

Accordingly, it as been recognized that the local impedance of a catheter electrode changes significantly based on its relative position to the sheath 8. For instance, FIGS. 3A, 3B and 3C illustrate three relative positions of a distal end of a catheter 14 to a sheath 8. As shown in FIG. 3A, the catheter 14 is fully encased with the sheath 8. In FIG. 3B a tip surface of the catheter 14 is extending beyond the distal end of the sheath 8. As shown, this tip surface of the catheter 14 is formed by the tip electrode 20 that is connected to the catheter 14. In FIG. 3C, the catheter 14 is extended further beyond the sheath 8 such that the tip electrode 20 is disposed entirely beyond the sheath. Of note, FIG. 3C also illustrates the plurality of ring electrodes 22 disposed along a portion of the length of the catheter 14.

As noted, the local impedance of the tip electrode 20 (or any other electrode) varies significantly based on its surroundings. For instance, when the tip electrode 20 is fully encased in the sheath, as shown in FIG. 3A, the tip electrode 20 may have, for example, a local impedance of 300 Ohms. When partially exposed, as shown in FIG. 3B, the tip electrode 20 may have a local impedance of 100 Ohms. Finally, when entirely exposed from the sheath 8, as shown in FIG. 3C, the tip electrode 20 may have a local impedance of 70 Ohms. In this regard, there is an impedance difference of over 4:1 between the condition where the tip electrode 20 is encased within the sheath 8 and where the tip electrode 20 has completely exited the sheath 8. Accordingly, by monitoring the impedance of the tip electrode 20, an indication of the location of the distal end of the catheter 14 relative to the distal end of the sheath 8 may be provided. Further, such an indication may be provided utilizing existing componentry (e.g., electrodes) of the catheter 14.

Figure 4:
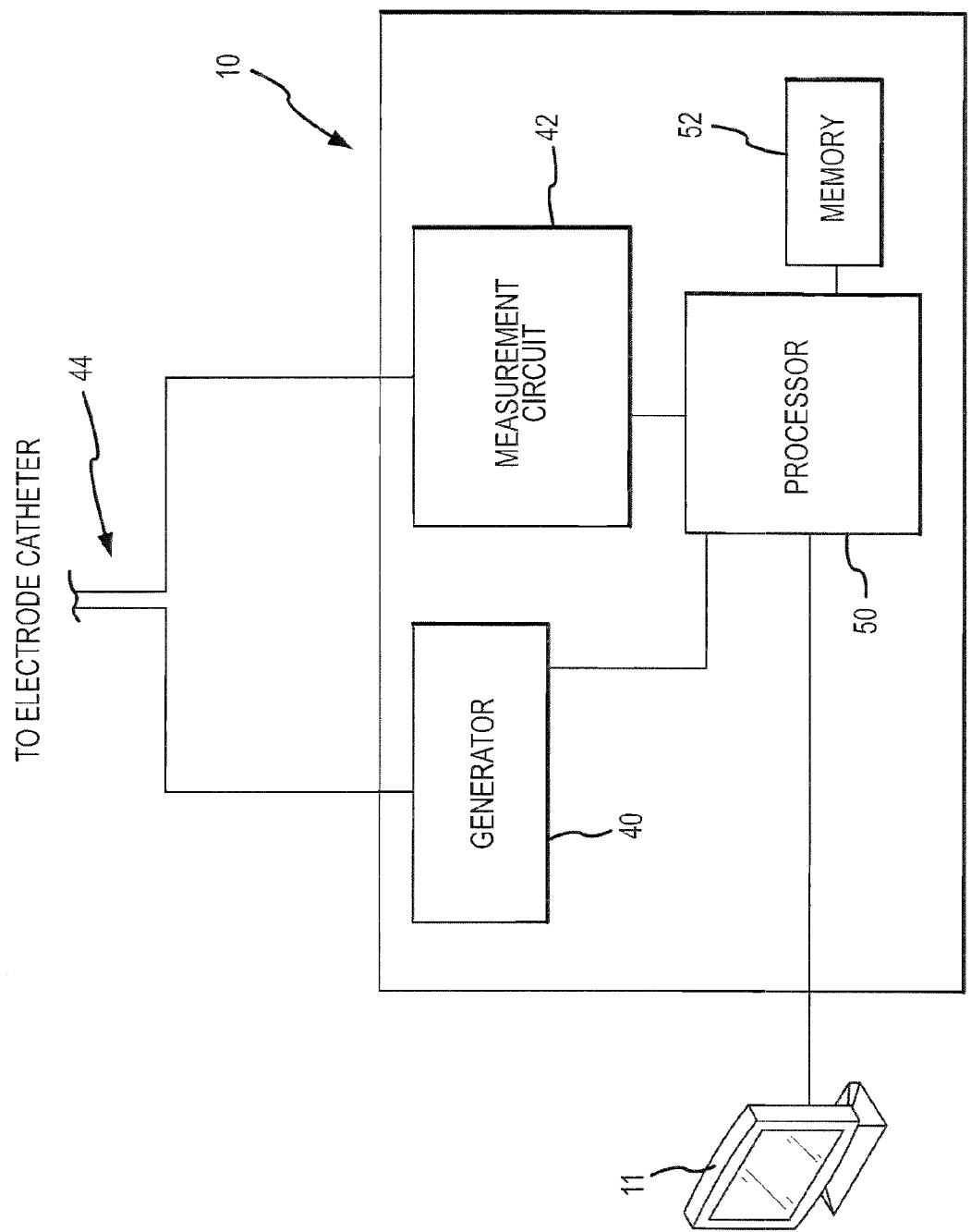
FIG. 4 is functional block diagram showing the exemplary catheter system of FIG. 1 in more detail.

FIG. 4 is a high-level functional block diagram showing the catheter system 10 in more detail as it may be implemented to assess position of the electrode catheter 14 relative to the distal end of the sheath 8. It is noted that some of the components typical of conventional tissue ablation systems are shown in simplified form and/or not shown at all in FIGS. 1 and 4 for purposes of brevity. Such components may nevertheless also be provided as part of, or for use with the catheter system 10. For example, electrode catheter 14 may include a handle portion, a fluoroscopy imaging device, and/or various other controls, to name only a few examples. Such components are well understood in the medical devices arts and therefore further discussion herein is not necessary for a complete understanding of the invention.

The exemplary catheter system 10 may include a generator 40, such as, e.g., AC current generator and/or a radio frequency (RF) generator, which in the present embodiment provides an electrical signal(s) to the electrode(s) of the catheter 14 (as illustrated by wires 44) for electrode position measurement, electrode contact measurement and/or ablation purposes. A measurement circuit 42 is electrically connected to the tip electrode 20. The electrode catheter 14 may also be electrically grounded, e.g., through grounding patch 46 affixed to the patient's arm or chest (as shown in FIG. 1).

Generator 40 may be operated to emit electrical energy to the tip electrode 20 of catheter 14. Generally, frequencies from 1 KHz to 500 KHz are suitable for this measurement. The measurement circuitry may be part of an ablation generator system, however, the impedance measurement(s) may be made with low-level signals such as, for example, 10 micro-amps. The resulting impedance at the electrode in response to the applied signal may be measured or monitored on a continuous basis using the measurement circuit 42. In one embodiment, the measurement circuit 42 may be a conventionally available resistance-capacitance-inductance (RCL). Still other measurement circuits 42 may be implemented and the invention is not limited to use with any particular type or configuration of measurement circuit. In any case, the impedance measurements may be used to determine an indication of the position of the tip electrode 20 (or other electrode) in relation to the sheath 8. This position may then be conveyed to the user in real-time to indicate, for example, if an electrode is exposed such that a mapping procedure may continue.

In an exemplary embodiment, the measurement circuit 42 may be operatively associated with a processor 50 and memory 52 to analyze the measured impedance. By way of example, processor 50 may determine an initial impedance at a catheter position that is known to be within the sheath 8. The processor may then sample subsequent impedance measurements to determine a change of the measured impedance. In an exemplary embodiment, impedance changes based on varying positions of, for example differently sized catheters, may be predetermined, e.g., during testing for any of a wide range of catheters and sheaths. The impedance changes may be stored in memory 52, e.g., as tables or other suitable data structures. The processor 50 may then access the tables or equations in memory 52 and determine a change in impedance (e.g., from an initial impedance) that indicates that the electrode is at least partially or fully exposed outside of the sheath. An indication of the relative position may be output for the user, e.g., at display device 54. As will be appreciated, the process may also be reversed to determine when a catheter has been withdrawn into a sheath.

In a further exemplary embodiment, the generator 40 may be operated to emit electrical energy, e.g., electrical signals, to the tip electrode 20 and at least one of the ring electrodes 22. For instance, the generator 40 may emit separate drive signals to the tip electrode 20 and the first ring electrode 22a. See for example FIG. 3C. The resulting impedance at each electrode 20, 22a in response to the applied signals may be measured using the measurement circuit 42. In such an embodiment, initial impedance values of the two electrodes 20, 22a, e.g., when fully disposed within the sheath 8, may be identified. Accordingly, the processor may generate a relative value of the impedances of the first and second electrodes 20, 22a. If an impedance of one of the electrodes subsequently changes, for example in conjunction with movement of the catheter, the impedance of the other electrode may remain substantially the same. In this instance, the relative value of the impedances may change. Accordingly, if the relative output changes by a sufficient degree, the processor may generate an output for the display.

Figure 5:
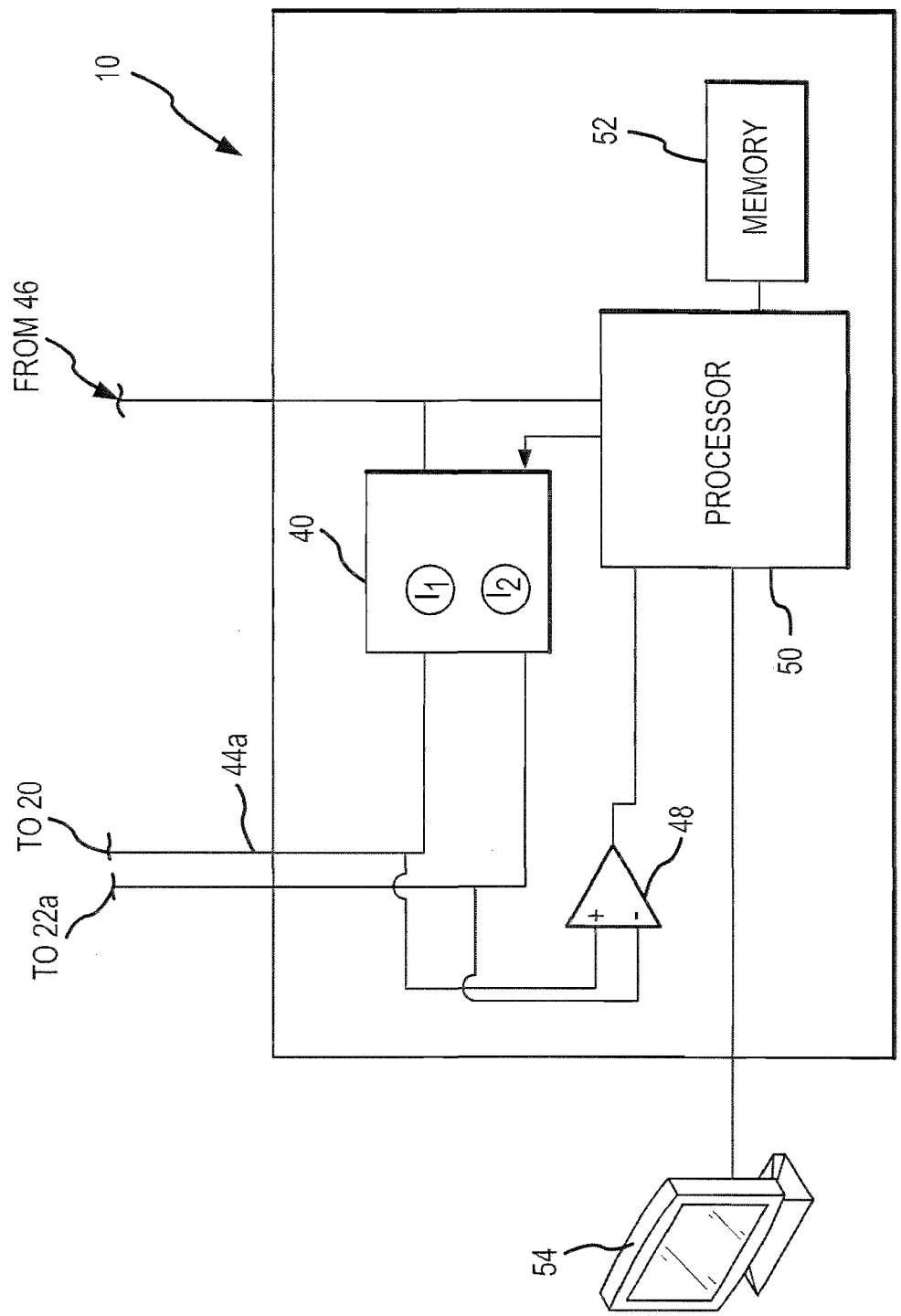
FIG. 5 is a functional diagram of an impedance determination circuit.

FIG. 5 illustrates another exemplary embodiment of a system for monitoring local impedance of one or more electrodes of a catheter. In this exemplary embodiment, impedance is not measured directly, rather, it is demodulated from the electrical signal provided to the electrode. As shown, one method is to pass a low level AC current, for example, 10 micro-amps at 40 kHz, through the electrode to be analyzed. In this regard, the generator 40 may provide the desired electrical signal $I_1$ to the tip electrode 20. As will be discussed herein, the generator 40 may also provide additional electrical signals to additional electrodes. The return path for electrical signal $I_1$ applied to the tip electrode is conveniently a body surface electrode, such that no other intra-cardiac electrodes are required for implementation. A differential amplifier 48 is provided for use in determining an indication of the impedance of the electrode being analyzed. Accordingly, an amplifier input is also connected to the analyzed electrode via a tap on the wire 44a carrying the electrical signal $I_1$ to the tip electrode 20. The amplifier is referenced to the body surface electrode 46 or to another body surface electrode. The resulting amplitude measured on the tip electrode 20, or other electrode as the case may be, may be recovered by synchronous demodulation of the driven current frequency from circuitry (e.g., processor 50) subsequent to the amplifier 48. The results of the demodulated signal will primarily reflect the very local ambient impedance of the electrode. The far field impedance of the current returning to the body surface will be very small because it is greatly spread out. The net result is that the demodulated signal/measured value is highly weighted toward the impedance of the electrode-fluid interface and bulk impedance immediately surrounding the electrode 20. Accordingly, the measured value may be monitored to identify changes that indicate the tip electrode 20 is entering or exiting the sheath.

Figure 6:
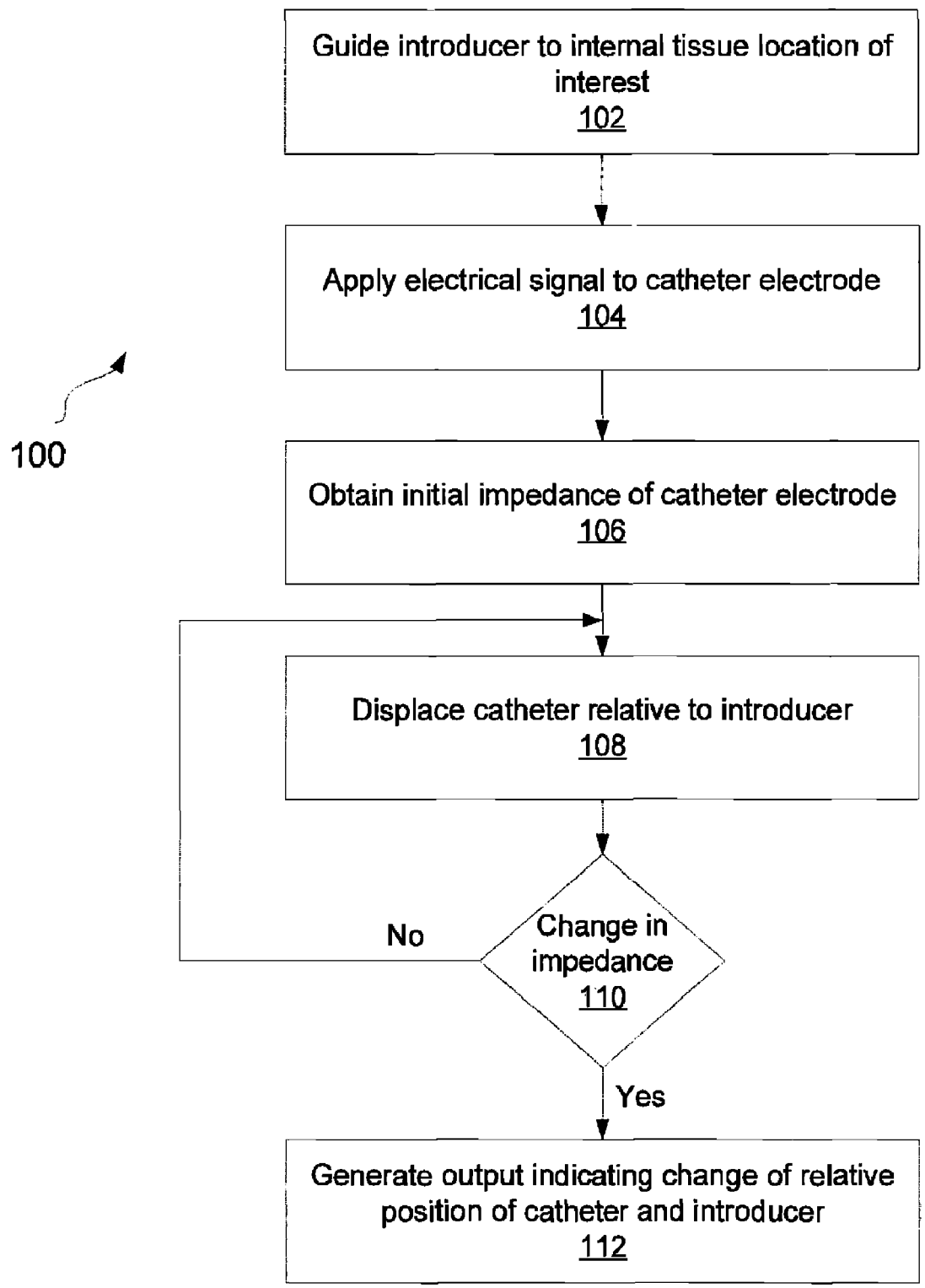
FIG. 6 illustrates one embodiment of a protocol that may be used to assess local impedance of a catheter electrode.

FIG. 6 illustrates one embodiment of a sheath exit sensing protocol 100 to determine when a catheter including at least one electrode exits a sheath of a guiding introducer. Initially, a sheath of a guiding introducer is guided (102) to an internal tissue location of interest. For instance, the sheath may be guided to a chamber of a patient's heart. Once the sheath is properly positioned, an electrical signal may be applied (104) to an electrode of a catheter disposed within an internal lumen of the sheath. Further, an initial impedance of the electrode in response to the electrical signal may be measured (106). Such measurement may be a direct measurement as discussed in relation to FIG. 4 or an indirect measurement as discussed in relation to FIG. 5. The catheter may be displaced (108) relative to the sheath while the impedance of the electrode is monitored (110). If a predetermined change in the impedance is detected, an output (112) indicating a change in the relative position of the electrode to the sheath may be provided. For instance, and output indicating the electrode has partially passed or fully passed out of the introducer may be provided to a display.

Figure 7:
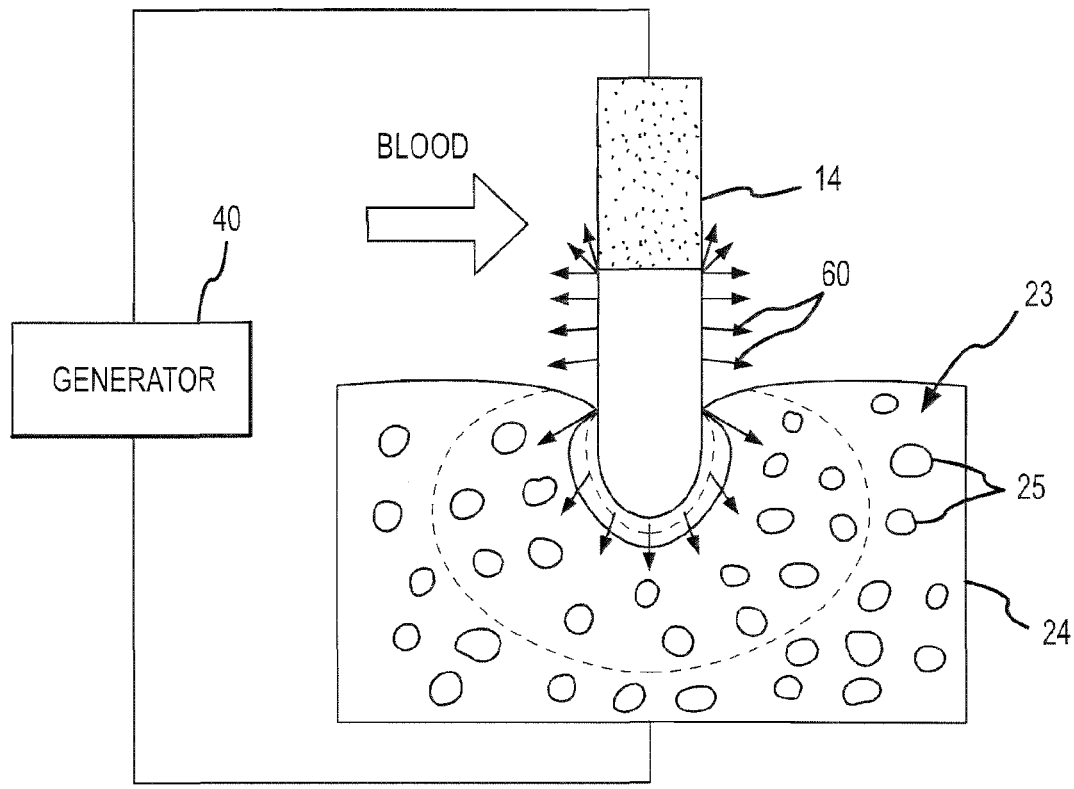
FIG. 7 is an exemplary block diagram showing impedance measurement for contact sensing and tissue sensing.

In addition to utilizing local impedances to identify changes in surrounding structure, such local impedances may also be utilized to calibrate a catheter for contact assessment. As will be appreciated, it generally known that contact impedance of an electrode may be utilized to determine if endocardial contact is achieved or how vigorous the contact is relative to, for example a catheter born electrode free floating in blood (e.g., in a heart chamber). Assessing a contact or coupling condition between the electrode catheter 14 and target tissue 24 based on impedance measurements at the electrode-tissue interface may be better understood with reference to FIGS. 7 and 7a. FIG. 7 is a model of the electrode catheter 14 in contact with (or coupled to) target tissue (e.g., specific myocardium tissue 24). The electrode catheter 14 is electrically connected to the generator 40 (e.g., an RF generator). In an exemplary embodiment, the circuit may be completed through the target myocardium tissue 24, showing that current flows through the blood, myocardium, and other organs to the reference electrode, such as a grounding patch 46 on the patient's body. See FIG. 1.

As described above, the generator 40 may be operated to generate electrical energy for emission by the electrode catheter 14. Emissions are illustrated in FIG. 7 by arrows 60. To avoid a risk of inducing an arrhythmia during contact or coupling assessment, it is desirable to use a low amount of current and power. A presently preferred range for frequencies between 1 KHz and 500 KHz and a current less than 10 micro-amps.

The frequency choice is mostly based on physiological aspect and engineering aspect and is within the purview of one of ordinary skill in the art. For physiological aspect, lower frequencies can introduce measurement errors due to electrode-electrolyte interface. When frequency goes higher to MHz range or above, the parasitic capacitance can become significant. It is noted, however, that the invention is not limited to use at any particular frequency or range of frequencies. The frequency may depend at least to some extent on operational considerations, such as, e.g., the application, the type of target tissue, and the type of electrical energy being used, to name only a few examples.

Figure 7A:
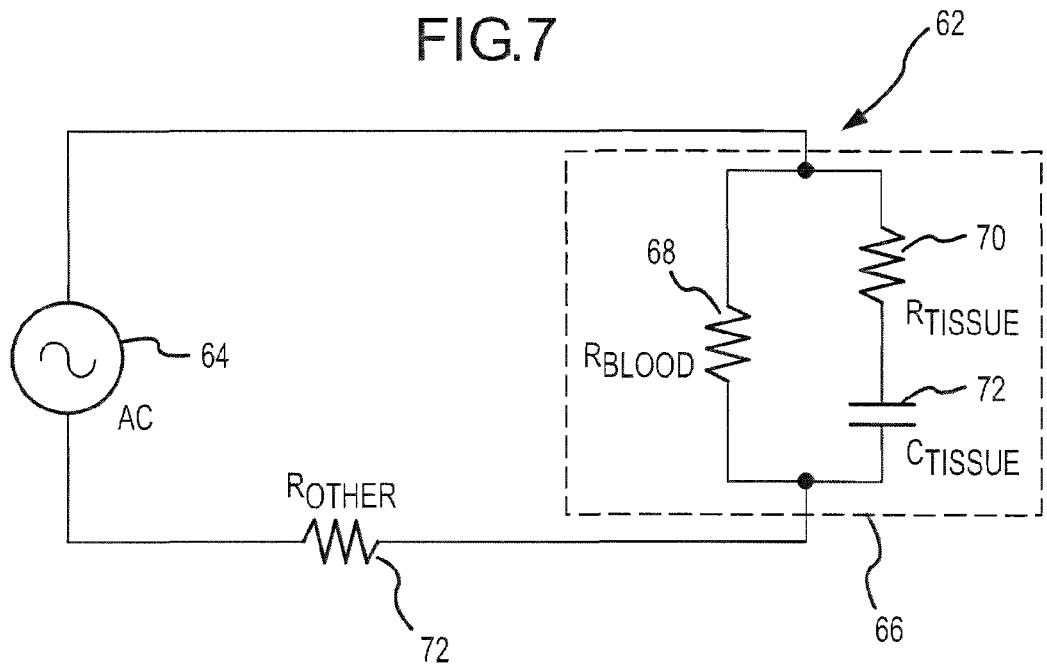
FIG. 7a is a circuit equivalent of the block diagram of FIG. 7.

Assuming, that a desired frequency has been selected for the particular application, the model shown in FIG. 7 may be further expressed as a simplified electrical circuit 62, as shown in FIG. 7a. In the circuit 62, generator 40 is represented as an AC source 64. The capacitance and resistance at the blood-tissue interface dominate impedance measurements at low frequency operation such as may be used for assessing electrode-tissue contact. Accordingly, other capacitive, inductive, and resistive effects may be ignored and the capacitive-resistive effects at the blood-tissue interface may be represented in circuit 62 by a resistor-capacitor (R-C) circuit 66.

The R-C circuit 66 may include a resistor 68 representing the resistive effects of blood on impedance, in parallel with a resistor 70 and capacitor 72 representing the resistive and capacitive effects of the target tissue 24 on impedance. When the electrode catheter 14 has no or little contact with the target tissue 24, which may include interstitial fluid spaces 23 and/or cell membranes 25, resistive effects of the blood affect the R-C circuit 66, and hence also affect the impedance measurements. As the electrode catheter 14 is moved into contact with the target tissue 24, however, the resistive and capacitive effects of the target tissue 24 affect the R-C circuit 66, and hence also affect the impedance measurements.

The effects of resistance and capacitance on impedance measurements may be better understood with reference to a definition of impedance. Impedance (Z) may be expressed as:

$$Z = R + jX$$

where:
R is resistance from the blood and/or tissue;
j an imaginary number indicating the term has a phase angle of +90 degrees; and
X is reactance from both capacitance and inductance.

It is observed from the above equation that the magnitude of the reactance component responds to both resistive and capacitive effects of the circuit 62. This variation corresponds directly to the level of contact or coupling at the electrode-tissue interface, and therefore may be used to assess the electrode-tissue contact or coupling. By way of example, when the electrode catheter 14 is operated at a frequency of 100 kHz and is primarily in contact with the blood, the impedance is purely resistive and the reactance (X) is close to 0 Ohms. When the electrode catheter 14 contacts the target tissue, the reactance component becomes negative. As the level of contact or coupling is increased, the reactance component becomes more negative.

Measurement circuitry may be designed to measure either or both components (R and/or X) of the above-noted equation, or equivalently their complex arithmetic equivalents: the magnitude and phase angle. When in the blood pool, the measurement almost entirely comprises resistance, whereas, particularly at higher contemplated frequencies, there is a small but discernable capacitive component when an electrode contacts a tissue boundary. The techniques taught herein may be applied using the resistive, reactive, magnitude, or phase angle of impedance.

Considering just the resistive component and ignoring the electrode impedance effects per se for a spherical electrode, (e.g., the distal end of tip electrode 20), the contact impedance is resistive and can be approximates as:

$$\rho/(4\pi r)$$

where r is the radius of the electrode and ρ is the medium resistivity of blood in this case.

If 20% of the electrode is in contact with tissue having a resistivity of three times that of blood, the impedance of the electrode 20 will increase by about 15%. This can be calculated by treating the apparent resistance of the two surfaces as parallel resistances. Such a change of impedance may be detected and an output indicative of such contact may be generated. However, in an instance where the tissue is only twice as resistive as the blood, a 20% contact of the electrode with the tissue will only result in about an 11% increase of the impedance of the electrode 20. In such instances of smaller increases due to contact, the impedance increases may fall into an expected variance range of impedance values.

As will be appreciated, the local impedance of the surrounding blood varies based on one or more physiological factors. One such factor is the cardiac stroke signal, which may cause changes of 5%-10% of the base impedance. That is, impedance may change throughout the cardiac cycle. Resistivity also changes some with ventilating and or flow rate of blood. Thus, resistivity of blood in the above equation cannot be relied on to be a constant. Further, failure to account for such physiological factors or 'local variance' may result in false positive and/or false negative indications of electrode-tissue contact.

Figure 8A:
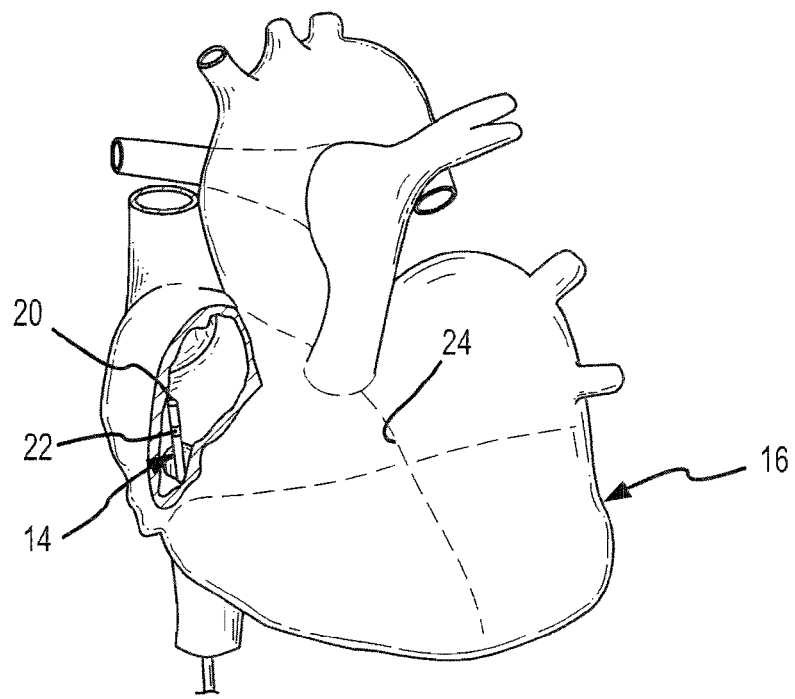
FIG. 8a illustrates an electrode catheter disposed in blood pool out of tissue contact for calibration.
Figure 8B:
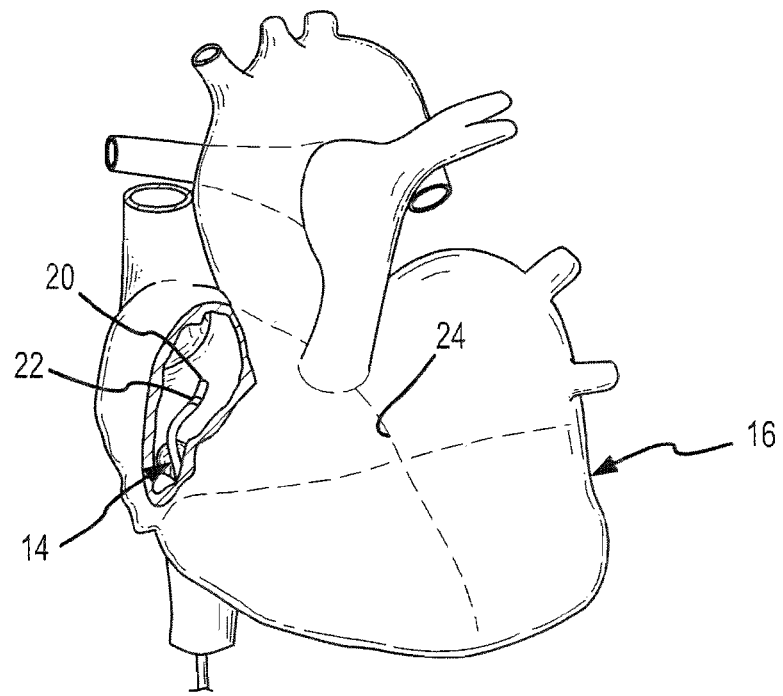
FIG. 8b illustrates an electrode catheter contacting patient tissue after calibration.

Utilizing the system outlined above in relation to FIG. 5 a process is provided that that independently samples the local resistivity in essence and dynamically cancels changes in it. The method further cancels common mode noise and impedance thereby affording a contact sensor that produces fewer false positive/negative contact indications. In this regard, the system may be calibrated to account for variances in local impedance. The method is outlined in relation to FIGS. 5, 8a and 8b. As illustrated in FIG. 5 two current sources $I_1$ and $I_2$ are provided which provide electrical signals to the tip electrode 20 and a ring electrode 22. These current sources $I_1$ and $I_2$ are of identical frequency and phase and at least one of the current sources $I_1$ and $I_2$ has a programmable or trimmable amplitude. One source ($I_1$) is connected to the electro-cardio electrode, whose contact status is desired, for example tip electrode 20, and the second source ($I_2$) is connected to a reference electrode, for example ring electrode 22a, which is ideally within 2-20 mm of the tip electrode 20. The current for the two sources may be returned to a common patch on the body surface as shown, or it may be returned to a blood pool electrode. Since sensing is not done on this return electrode, local resistivity changes in its proximity will have no impact. Further, the differential amplifier 48 can be set to high gain in this method, maximizing common mode rejection and minimizing noise.

In-vitro or in-vivo at the start of a study, a calibration is done with the catheter 14 away from a wall or boundary. See FIG. 8a. The calibration consists of trimming or programming one of the current sources $I_1$ and $I_2$ until commonly zero volts are demodulated from the impedance circuit. Thus, if the tip electrode 20 has a larger surface area than the ring electrode 22a, $I_1$ may be trimmed to deliver more current such that the potential created equals that from $I_2$ driving the ring electrode 22a. With this calibration, local resistivity changes common to both electrodes are now be cancelled out. Now only when electrode 20 or 22a incurs a change, such as contact, and the other does not, will a potential register out of the impedance circuit. Accordingly, when such a potential is identified, this contact may be registered with, for example, a visualization and/or navigation system. Of note, it may be beneficial to implement the system with a segmented ring electrode that is electrically divided into, for example, three or four segments. If separate differential measurements are made between the tip electrode and each segment, then in the case of a catheter laying along tissue, at least one of the segments of the segmented ring electrode may not be contacting tissue. That is, one or more segments may be facing the fluid/blood pool. IF the tip electrode is contacting the tissue, a high differential will register between the tip electrode and the blood facing segment(s). This may provide a robust indication of contact. A similar system may be implemented using spot electrodes.

Such 'local normalization' may be performed when the catheter is disposed near a contact surface (e.g., within a fluid/blood pool), which may be determined using a substantially real-time model as discussed above. Generally, the differential of the electrode outputs will be small but may be non-zero at this location. However, before an operator (or robotic system) makes a move to contact the surface, this 'offset' may be measured and subsequently subtracted as the catheter approaches the surface for ablation or other purposes. This removal of the offset value reduces the likelihood of false positives or negatives occurring when utilizing the tip electrode (or other electrode) as an endocardial surface contact sensor.

Figure 9:
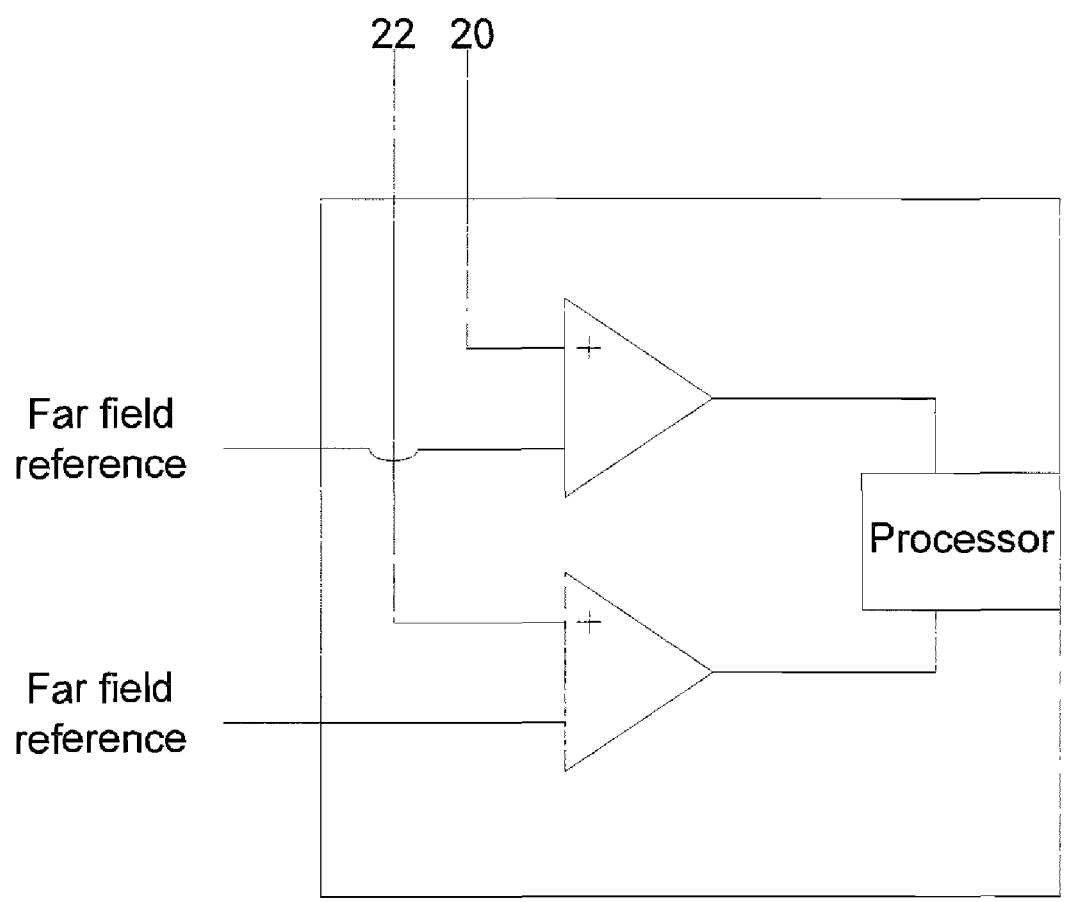
FIG. 9 illustrates a measurement circuit for single ended measurement of first and second electrodes.

In another exemplary embodiment, a further system and method for accounting for local variance is provided. As illustrated in FIG. 9, single ended measurements are made for separate electrodes of the catheter. For instance, a first measurement T is made for the tip electrode 20 and a second measurement R is made for a ring electrode. The measurements may be made individually utilizing different amplifier circuitry as shown. In such an arrangement, subsequent processing may be performed digitally (e.g., in software). In any case, the measurements T and R may be utilized to calibrate the system for subsequent contact sensing. In this regard, a differential may be determined for the electrodes in a blood pool. For instance:

$$D_b = T_b - R_b \approx 0$$

In this regard, one of the measurements may be weighted (e.g., scaled) relative to the other measurement such the differential is substantially zero. At the same time, a common mode or nominal average may be computed:

$$A_b = (T_b + R_b)/2$$

Going forward, the average of the blood pool $A_b$ may be utilized to normalize subsequent measurements. For instance:

$$(A_b/A)^x \cdot D$$

The value x may be 1.0 or any other value that optimizes sensitivity. D is the differential value. In this instance, if the average value of A increases substantially (e.g., due to tissue contact of one of the electrodes) relative to the calibration value (i.e., $A_b$) the results may be derated. The system further minimizes sensitivity to false positives. With this system, the higher the average value, the less weight is applied to the difference. While such derating may be linear with the exponent x=1 in the above equation, non-linear equations may be utilized as well.

Figure 10:
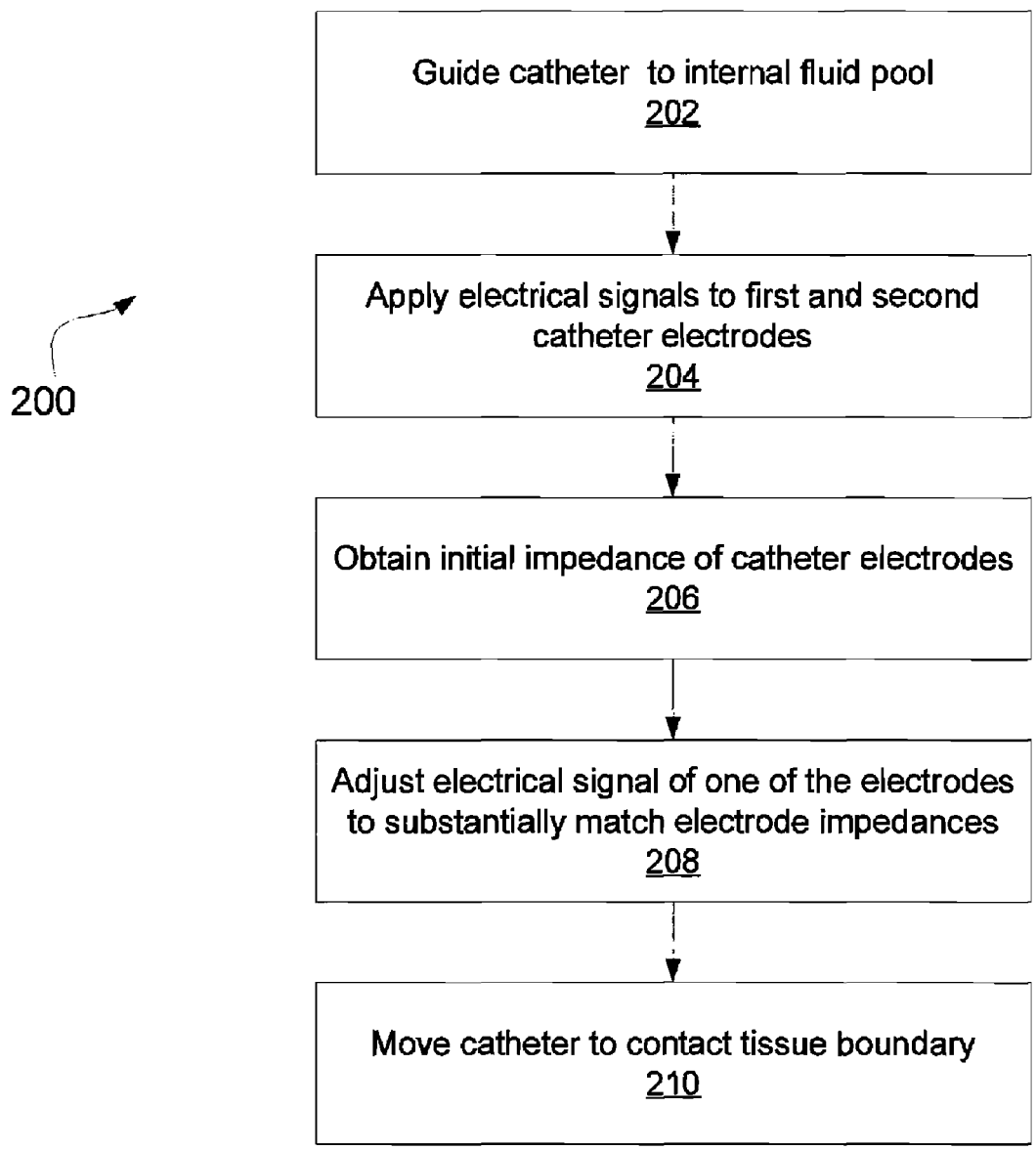
FIG. 10 illustrates one embodiment of a protocol that may be used to calibrate an electrode catheter for local variances.

FIG. 10 illustrates one embodiment of a calibration protocol (200) for calibrating an electrode catheter for local variance. Initially, a catheter having at least first and second electrodes is guided (202) to a fluid pool that is out of contact with a boundary of the fluid pool. See FIG. 8a. Such guiding may be assisted by various imaging devices. Individual electrical signals may be applied (204) to the electrodes and an initial impedance of the first and second electrodes may be obtained (206). This may entail directly measuring the impedance of each electrode, indirectly measuring the impedance of each electrode and/or identifying a relative/differential impedance of the electrodes. One of the electrical signals may be adjusted (208) to substantially match or equalize the impedance of the two electrodes. Once the impedances are matched, the catheter is calibrated and may be moved into contact (210) with patient tissue. See FIG. 8b.

Although three embodiments of a process for detecting local impedance and two applications of the measured local impedance have been described above with a certain degree of particularity, those skilled in the art could make numerous alterations to the disclosed embodiments without departing from the spirit or scope of this invention. For example, it will be appreciated that the other circuits may be designed for detecting/measuring a local impedance of a catheter electrode. However, an important feature of this invention is the recognition that this local impedance changes based on the surroundings of the electrode. In this regard, such changes may be utilized for other applications. For instance, indications of a change of impedance may be utilized to guide a catheter into small volume structure (e.g., veins or arteries) from larger volume structure (e.g., heart chambers) or vice versa. Further, it will be noted that all directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for performing a medical procedure, comprising the steps of:
    guiding a catheter to an internal patient location, wherein the catheter includes at least first and second electrodes;
    providing first and second separate electrical signals having equal frequency and phase to the first and second electrodes, respectively, wherein an amplitude of one of the first and second electrical signals is adjustable relative to an amplitude of the other of the first and second electrical signals;
    monitoring the first and second electrical signals as applied to the first and second electrodes, respectively, to identify first and second input responses;
    adjusting the amplitude of at least one of the first and second electrical signals as applied to a corresponding one of the electrodes to generate an initial relative response of the first and second electrodes;
    identifying a level of the initial relative response;
    identifying a change in the initial relative response;
    scaling the change based on the level of the initial relative response to generate a scaled change of response; and
    generating an output based on the scaled change of response.

2. The method of claim 1, wherein a return path for the electrical signals is via an external electrode.

3. The method of claim 1, wherein the step of generating an initial relative response further comprises:
    identifying a first impedance for the first electrode and identifying a second impedance for the second electrode.

4. The method of claim 1, further comprising:
    providing a plurality of separate electrical signals to a plurality of electrodes, respectively;
    identifying relative responses between one of the plurality of electrodes and at least two other electrodes, wherein the output is generated based on a change of at least one of the relative responses.

5. The method of claim 1, wherein the output indicates a contact condition with tissue.

6. The method of claim 1, further comprising:
    adjusting the amplitude of the one electrical signal to substantially match the first and second input responses of the first and second electrodes to the first and second electrical signals, respectively.

7. The method of claim 6, wherein the step of adjusting is performed while the first and second electrodes are in a fluid pool.

8. The method of claim 7, further comprising:
    moving the catheter to contact at least one of the electrodes with a wall of the internal patient location
    wherein generating an output comprises generating a contact response of the electrode contacting the wall.

9. The method of claim 8, further comprising:
    in conjunction with generating the contact response, registering information with a location system.

10. The method of claim 8, further comprising:
    assessing contact between the catheter and the wall based on the contact response.

11. The method of claim 1, wherein the step of identifying the relative responses comprises:
    generating a differential of the first and second electrical signals.

12. The method of claim 11, wherein the step of generating the differential comprises:
    individually measuring input responses of the first and second electrodes; and
    identifying a difference between the responses.

13. The method of claim 11, wherein the step of generating the differential comprises:
    demodulating a combination of the first and second electrical signals as applied to the electrodes, wherein demodulating is based at least in part on a frequency of one of the first and second electrical signals to produce the differential.

14. The method of claim 11, further comprising:
    adjusting one of the electrical signals to adjust the differential.

15. A method for performing a medical procedure, comprising the steps of:
    positioning a catheter within an internal patient location, wherein the catheter includes a plurality of electrodes;
    providing a plurality of separate electrical signals to the plurality of electrodes disposed at the internal patient location, respectively;
    monitoring the plurality of electrical signals as applied to the plurality of electrodes, respectively, to identify a plurality of impedances;
    adjusting an amplitude of at least one of the electrical signals as applied to at least one of the electrodes relative to at least one of the other electrical signals to match impedances of at least two of the plurality of electrodes while the electrodes are free of contact with a wall of the internal patient location;

identifying a level of an initial response of the electrodes having matching impedances;

identifying a change in the impedance of one of the electrodes;

scaling the change based on the level of the initial response to generate a scaled change of impedance; and assessing contact between the catheter and the wall based on the scaled change of impedance.

16. The method of claim 15, wherein the step of adjusting comprises:

adjusting an amplitude of at least one of the plurality of electrical signals.

17. The method of claim 15, further comprising:

registering contact information associated with the contacting with a location system.

18. An apparatus for performing a medical procedure, comprising:

means for providing a plurality of separate electrical signals to a plurality of electrodes of a catheter disposed at an internal patient location, respectively;

means for monitoring the plurality of electrical signals as applied to the plurality of electrodes, respectively, to identify a plurality of impedances;

means for adjusting an amplitude of at least one of the electrical signals as applied to at least one of the electrodes relative to at least one of the other electrical signals to match impedances of at least two of the plurality of electrodes while the electrodes are free of contact with a wall of the internal patient location;

means for identifying a level of an initial response of the electrodes having matching impedances;

means for identifying a change in the impedance of one of the electrodes;

means for scaling the change based on the level of the initial response to generate a scaled change of impedance; and means for assessing contact between the catheter and the wall based on the scaled change of impedance.

19. The apparatus of claim 18, wherein the means for adjusting is further operative to adjust an amplitude of at least one of the plurality of electrical signals.

20. The apparatus of claim 18, further comprising:

a location system for registering contact information associated with the contacting.

* * * * *